United States Patent [19]

Fujita et al.

[11] 4,310,693
[45] Jan. 12, 1982

[54] O-AMINOPHENOL COMPOUNDS

[75] Inventors: Shinsaku Fujita; Koichi Koyama; Yoshio Inagaki, all of Minami-ashigara, Japan

[73] Assignee: Fuji Photo Film Co., Ltd., Minami-ashigara, Japan

[21] Appl. No.: 170,234

[22] Filed: Jul. 18, 1980

[30] Foreign Application Priority Data

Jul. 18, 1979 [JP] Japan .................................. 54/91185
Jul. 18, 1979 [JP] Japan .................................. 54/91186

[51] Int. Cl.³ .................... C07C 149/42; C07C 87/60; C07C 91/40; C07C 103/87; C07C 103/29; C07C 103/22; C07C 103/26; C07C 103/34

[52] U.S. Cl. ..................................... 564/440; 564/443; 564/442; 260/152; 430/223; 260/162; 260/163; 260/198; 260/200; 260/206; 260/401; 260/404; 260/404.5; 260/465 D; 260/465 E; 564/153; 564/154; 564/158; 564/166; 564/174; 564/175; 564/180; 564/186; 564/202; 564/211; 564/218; 564/221; 564/222; 564/307; 564/308; 564/322; 564/426; 564/427; 564/428; 564/430; 564/441

[58] Field of Search ............... 564/443, 440, 307, 308, 564/430

[56] References Cited

U.S. PATENT DOCUMENTS 3,666,812  5/1972  Kalopissis et al. .................. 564/443

FOREIGN PATENT DOCUMENTS 48-33826  5/1973  Japan ................................. 564/443
51-113624 10/1976  Japan ................................. 564/443
53-149328 12/1978  Japan ................................. 564/443

Primary Examiner—John Doll
Attorney, Agent, or Firm—Sughrue, Mion, Zinn, Macpeak and Seas

[57] ABSTRACT o-Aminophenol derivatives are described represented by the formula (I)

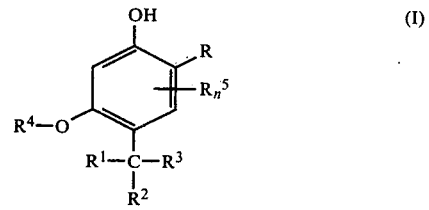

wherein R represents $-NH_2$ or $-NH-CO-R^6$; $R^1$ and $R^2$ which may be the same or different, each can represent an alkyl group or an aromatic group, or $R^1$ and $R^2$ together can form a ring; or $R^1$, $R^2$ and $R^3$ together can form a ring ; $R^3$ represents hydrogen, an alkyl group or an aromatic group; $R^4$ can represent an alkyl group or an aromatic group; $R^5$ can represent an alkyl group, an alkoxy group, an alkylthio group, an arylthio group, a halogen atom or an acylamino group; and n is 0, 1 or 2; $R^6$ represents an alkyl group or an aromatic group; and $R^4$ and $R^5$ together can form a heterocyclic ring, $R^1$ and $R^4$ together can form a heterocyclic ring, or $R^1$ and $R^5$ together can form a ring; and $R^1$, $R^2$, $R^3$, $R^4$, and $R^5_n$ have a total of 7 or more carbon atoms.

7 Claims, No Drawings

O-AMINOPHENOL COMPOUNDS

BACKGROUND OF THE INVENTION

1. Field of the Invention

This invention relates to synthetic intermediate compounds useful in preparing color photosensitive materials. More particularly, it relates to intermediate compounds for producing compounds which release a diffusible dye by a redox reaction subsequent to development of silver halide.

2. Description of the Prior Art

A color diffusion transfer image-forming process which comprises using dye-releasing redox compounds (also often referred to as DRR compounds) has been described in Japanese Patent Application (OPI) No. 33826/73 (the term "OPI" as used herein refers to a "published, unexamined Japanese patent application"). The expression "dye-releasing redox compounds" used above is p-sulfonamidophenols (or p-sulfonamidonaphthols) in which a dye part and a nondiffusible phenol part (or naphthol part) are linked at the p-position (with respect to the aromatic —OH group) through a sulfonamido group. When a photosensitive silver halide emulsion coexistent with said compound is exposed to light and developed thereafter, the p-sulfonamidophenol or naphthol is oxidized corresponding to the developed silver halide content. It has been presumed that the resulting oxidation product is decomposed by attack of alkali processing solution to form a diffusible dye and nondiffusible benzoquinone or naphthoquinone, and that the resulting diffusible dye is transferred to an image-receiving layer. However, when using the above-described p-sulfonamidophenols, their dye-releasing efficiency is so low as to produce a sufficient transfer density. Furthermore, the above-described p-sulfonamidonaphthols produce yellow stains, because some p-naphthoquinone is left at the photosensitive layer side, even if a desilvering treatment is carried out after releasing the dye, and, consequently, residual color images on the photosensitive layer cannot be utilized as negative or positive images.

Dye-releasing redox compounds which are o-sulfonamidophenols substituted by an alkoxy group on the 4-position thereof have been described in Japanese Patent Application (OPI) No. 113624/76. These compounds have rather excellent properties as compared with the earlier prior art compounds, but it has been desired to further improve the dye-releasing ability of sulfonamidophenols. Also, dye-releasing redox compounds which are o-sulfonamidophenols having an alkoxy group at the 5-position and a methyl group at the 4-position have been described in Japanese Patent Application (OPI) No. 149328/78. However, it has been desired to further improve the dye-releasing ability of these sulfonamidophenols also.

SUMMARY OF THE INVENTION

A first object of this invention is to provide intermediates for novel dye-releasing redox compounds and a process for synthesizing them.

A second object is to provide intermediates for dye-releasing redox compounds which provide a high transfer density when used for diffusion transfer, and a process for synthesizing them.

A third object is to provide intermediates for dye-releasing redox compounds which form a residual dye image having less residual yellow color after releasing the dye, and a process for synthesizing such intermediates.

A fourth object is to provide intermediates for dye-releasing redox compounds having an excellent dye-releasing efficiency.

It has now been found that compounds represented by the formula (I) satisfy the above-described objects.

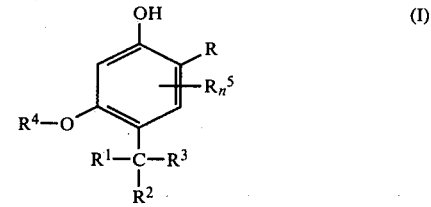

(I)

In formula (I), R represents $-NH_2$ or $-NH-CO-R^6$; $R^1$ and $R^2$, which may be the same or different, each can represent an alkyl group or an aromatic group, or $R^1$ and $R^2$ together can form a ring; or $R^1$, $R^2$, and $R^3$ together can form a ring; $R^3$ represents hydrogen, an alkyl group or an aromatic group; $R^4$ can represent an alkyl group or an aromatic group; $R^5$ can represent an alkyl group, an alkoxy group, an alkylthio group, an arylthio group, a halogen atom or an acylamino group; n is 0, 1 or 2; $R^6$ represents an alkyl group or an aromatic group; and $R^4$ and $R^5$ together can form a heterocyclic ring, $R^1$ and $R^4$ together can form a heterocyclic ring, or $R^1$ and $R^5$ together can form a ring; and $R^1$, $R^2$, $R^3$, $R^4$, and $R^5_n$ contain a total of 7 or more carbon atoms.

DETAILED DESCRIPTION OF THE INVENTION

With respect to the compounds of formula (I), preferred compounds are those represented by the formula (IA).

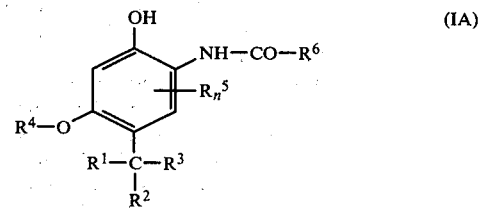

(IA)

In formula (IA), $R^1$, $R^2$, $R^3$, $R^4$, $R^5$, $R^6$, and n each have the same meaning as defined above for formula (I).

A preferred process for synthesizing the o-acylaminophenol compounds represented by the formula (IA) comprises reacting a compound represented by the formula (II)

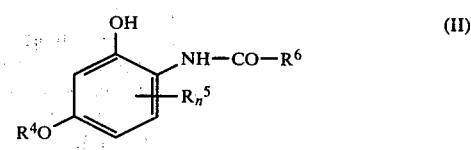

(II)

wherein $R^4$, $R^5$, $R^6$, and n each have the same meaning as defined in formula (IA), with a moiety represented by formula (III)

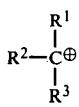

(III)

wherein $R^1$, $R^2$ and $R^3$ each have the same meaning as defined in the formula (IA).

Other preferred compounds according to formula (I) are those represented by formula (IB)

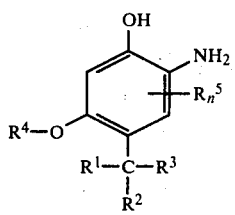

(IB)

wherein $R^1$, $R^2$, $R^3$, $R^4$, $R^5$ and n each have the same meaning as defined in formula (I).

Examples of the alkyl groups represented by $R^1$ and $R^2$ are those having from 1 to 40 carbon atoms, and preferably from 1 to 24 carbon atoms, which alkyl groups may be straight, branched or cyclic, and may be substituted by substituents (for example, an alkoxy group, a cyano group, a hydroxyl group, a halogen atom, a phenoxy group and a substituted phenoxy group, an acylamino group, etc.). Preferred examples of $R^1$ and $R^2$ include straight chain alkyl groups, such as a methyl group, an ethyl group, a propyl group, a butyl group, a pentyl group, a hexyl group, a heptyl group, an undecyl group, a pentadecyl group and a heptadecyl group, etc.; and branched chain alkyl groups such as an isopropyl group, an isobutyl group, a t-butyl group, a t-amyl group and a neopentyl group, etc. Examples of the aromatic groups represented by $R^1$ and $R^2$ include phenyl groups, substituted phenyl groups, naphthyl groups and substituted naphthyl groups. Examples of substituents in these substituted phenyl and naphthyl groups include an alkoxy group, a cyano group, a hydroxyl group, a nitro group, an alkyl group, etc. When $R^1$ and $R^2$ together form a ring, it is preferably a ring of from 5 to 40 members, and more preferably from 5 to 12 members (for example, —$CR^1R^2R^3$ represents cyclopentyl, cyclohexyl, cyclododecyl, etc.). When $R^1$, $R^2$ and $R^3$ together form a ring, it is preferably a bicyclic or tricyclic ring having from 7 to 40 carbon atoms and more preferably having from 7 to 12 carbon atoms (for example, —$CR^1R^2R^3$ is 1-adamantyl, etc.).

Examples of the alkyl groups represented by $R^3$ are those which have from 1 to 40 carbon atoms, and preferably from 1 to 24 carbon atoms, which may be straight, branched or cyclic and may be substituted by substituents (for example, an alkoxy group, a cyano group, a hydroxyl group, a halogen atom, a phenoxy group, a substituted phenoxy group, an acylamino group, etc.). Preferred examples of $R^3$ include straight chain alkyl groups such as a methyl group, an ethyl group, a propyl group, a butyl group, a pentyl group, a hexyl group, a heptyl group, an undecyl group, a pentadecyl group, a heptadecyl group, etc.; and branched alkyl groups, such as an isopropyl group, an isobutyl group, a t-butyl group, a t-amyl group, a neopentyl group, etc. Examples of the aromatic group represented by $R^3$ include a phenyl group, a substituted phenyl group, a naphthyl group and a substituted naphthyl group. Examples of substituents in these substituted phenyl and naphthyl groups include an alkoxy group, a cyano group, a hydroxyl group, a nitro group, an alkyl group, and so forth. In a more preferred embodiment, $R^3$ represents an alkyl group or aromatic group described above.

Examples of the alkyl groups represented by $R^4$ are those which have from 1 to 40 carbon atoms, and preferably from 1 to 24 carbon atoms, which may be straight, branched or cyclic and may be substituted by substituents (for example, an alkoxy group, a cyano group, a hydroxyl group, a halogen atom, a phenoxy group, a substituted phenoxy group, an acylamino group, etc.). Preferred examples of $R^4$ include straight chain alkyl groups such as a methyl group, an ethyl group, a propyl group, a butyl group, a pentyl group, a hexyl group, a heptyl group, an undecyl group, a pentadecyl group, a heptadecyl group, etc.; and branched chain alkyl groups, such as an isopropyl group, an isobutyl group, a t-butyl group, a t-amyl group, a neopentyl group, etc. Examples of the aromatic group represented by $R^4$ include a phenyl group, a substituted phenyl group, a naphthyl group, and a substituted naphthyl group. Examples of the substituents in the substituted phenyl group and naphthyl group include an alkoxy group, a cyano group, a hydroxyl group, a nitro group and an alkyl group and so forth.

The alkyl portion of the alkyl group, alkoxy group or alkylthio group represented by $R^5$ may have from 1 to 40 carbon atoms, and preferably has from 1 to 24 carbon atoms, which may be straight, branched or cyclic and may be substituted by substituents (for example, an alkoxy group, a cyano group, a hydroxyl group, a halogen atom, a phenoxy group, a substituted phenoxy group, an acylamino group, etc.). Preferred examples of $R^5$ include straight chain alkyl groups such as a methyl group, an ethyl group, a propyl group, a butyl group, a pentyl group, a hexyl group, a heptyl group, an undecyl group, a pentadecyl group and a heptadecyl group, etc.; and branched chain alkyl groups such as an isopropyl group, an isobutyl group, a t-butyl group, a t-amyl group, a neopentyl group, and so forth.

Preferred examples of the arylthio group represented by $R^5$ include a phenylthio group, a substituted phenylthio group and a heterocyclic thio group.

Typical examples of the acylamino group represented by $R^5$ include an alkyl-CONH- group and a (substituted or unsubstituted) phenyl-CONH- group.

Examples of substitutents of the above-described substituted phenyl group include an alkoxy group, a cyano group, a hydroxyl group, a nitro group, an alkyl group, and so forth.

$R^4$ and $R^5$ together, $R^1$ and $R^4$ together, and $R^1$ and $R^5$ together may form two or more rings simultaneously. When $R^4$ and $R^5$ form a heterocyclic ring, $R^5$ can be substituted at 3- or 6-position. However, formation of an aromatic hydrocarbon ring is not preferred because of causing color stain or residual parts. In more preferred embodiment, —$CR^1R^2R^3$, —$OR^4$ and —$R^5$ do not link each other.

Examples of the alkyl groups represented by $R^6$ are those which have from 1 to 40 carbon atoms, and preferably from 1 to 24 carbon atoms, which may be straight, branched or cyclic and may be substituted by substituents (for example, an alkoxy group, a cyano group, a hydroxyl group, a halogen atom, a phenoxy group, a substituted phenoxy group, an acylamino group, etc.). Preferred examples of $R^6$ include straight chain alkyl groups such as a methyl group, an ethyl group, a propyl group, a butyl group, a pentyl group, a hexyl group, a heptyl group, an undecyl group, a pentadecyl group, a heptadecyl group, etc.; and branched chain alkyl groups such as an isopropyl group, an isobutyl group, a t-butyl group, a t-amyl group, a neopentyl group, etc. Examples of the aromatic groups represented by $R^6$ include a phenyl group, a substituted phenyl group, a naphthyl group and a substituted naphthyl group. Examples of substituents in these substituted phenyl and naphthyl groups include an alkoxy group, a cyano group, a hydroxyl group, a nitro group and an alkyl group, and so forth.

As $R^6$, the methyl group is particularly preferred because the synthesis is thereby facilitated.

In a preferred embodiment, the compounds (IA) and (IB) of the invention are represented by the formulae (IV A) and (IV B), respectively.

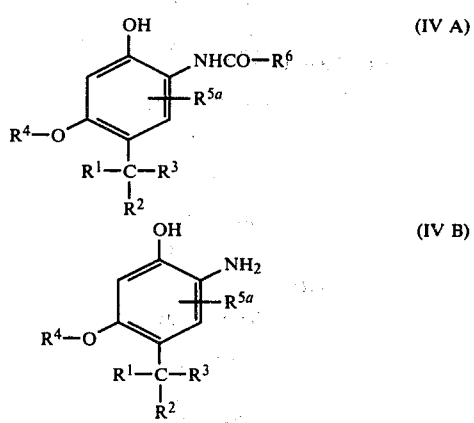

In formulae (IV A) and (IV B), $R^{5a}$ represents hydrogen or the same substitutents as $R^5$ in formula (I), and $R^1$, $R^2$, $R^3$, $R^4$, and $R^6$ represent each the same meaning as defined in the formula (I).

It is further preferred that

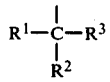

in the formulae (IV A) and (IV B) represents a t-alkyl or an aralkyl group, or cyclohexyl group, more preferably, a t-butyl group, a t-amyl group, a cyclohexyl group, a 1-ethyl-1-methylpentyl group, t-hexyl group, a t-octyl group,

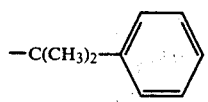

or 1-adamantyl group; that $R^4$ in the formulae (IV A) and (IV B) represents an unsubstituted alkyl grop or an aryloxyalkyl group (each of these groups is particularly preferred to have a total of from 1 to 24 carbon atoms); and that $R^{5a}$ in the formulae (IV A) and (IV B) represents hydrogen, an alkyl group or an alkoxy group, wherein each of these groups is preferred to have from 1 to 24 carbon atoms, more preferably $R^{5a}$ represents hydrogen or methyl group. $R^4$ and $R^5$ together, $R^1$ and $R^4$ together, and $R^1$ and $R^5$ together may form two or more rings simultaneously. In more preferred embodiment, $-CR^1R^2R^3$, $-OR^4$ and $-R^{5a}$ of the formulae (IV A) and (IV B) do not link each other.

Examples of compounds according to the invention are shown below.

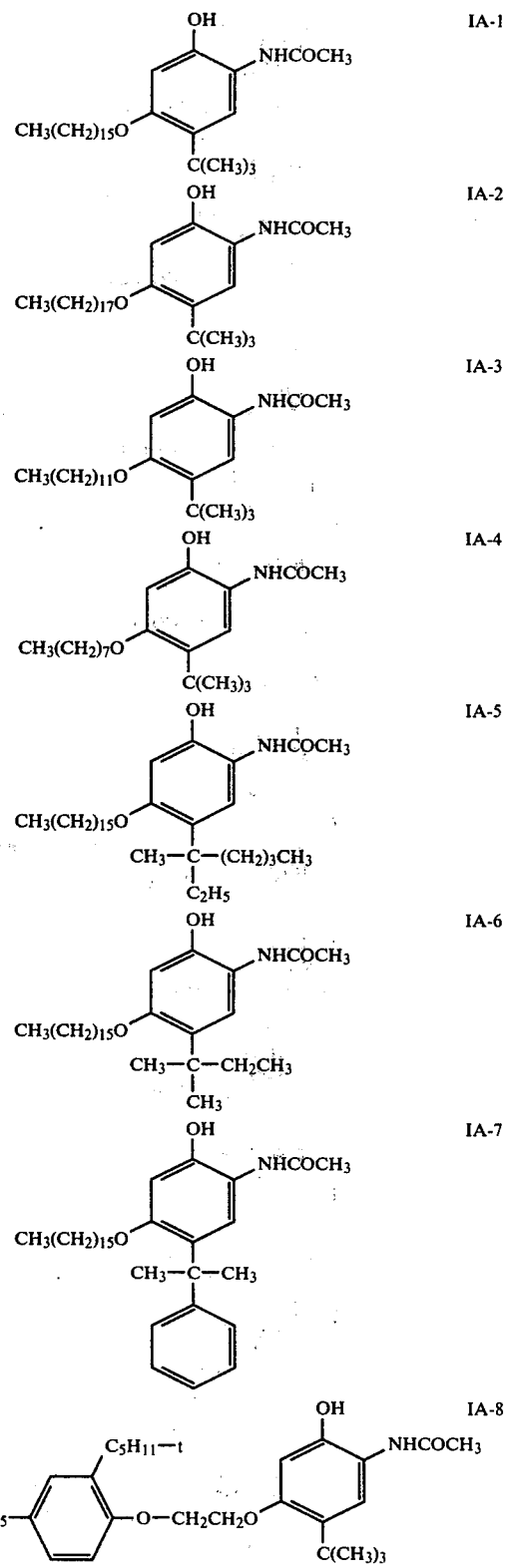

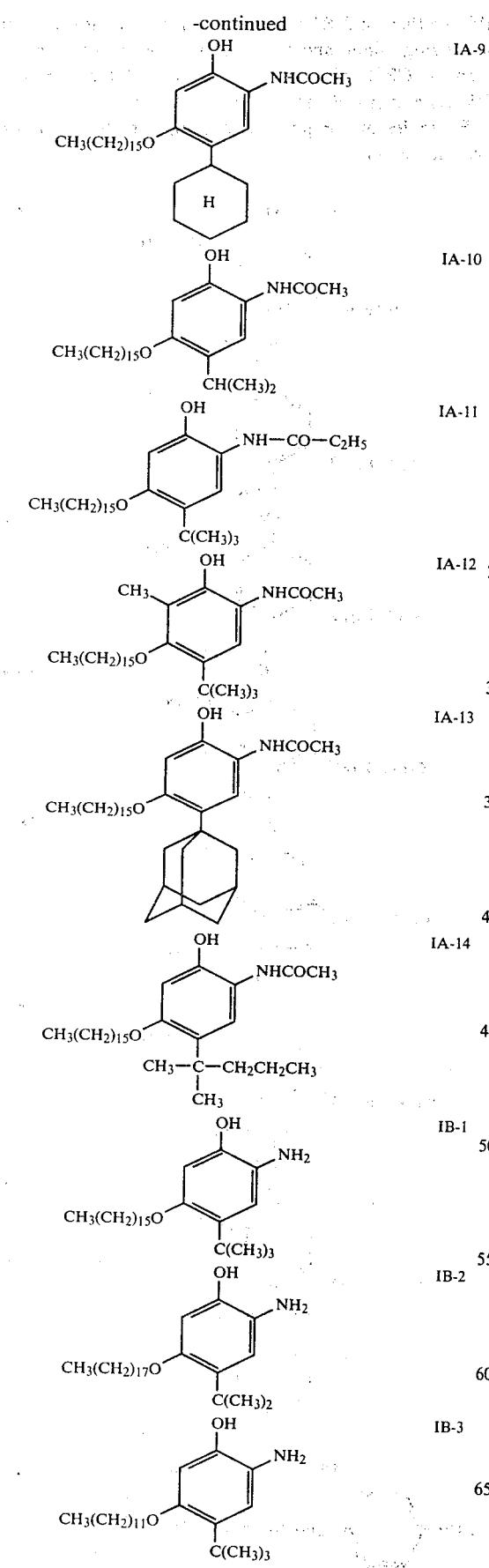
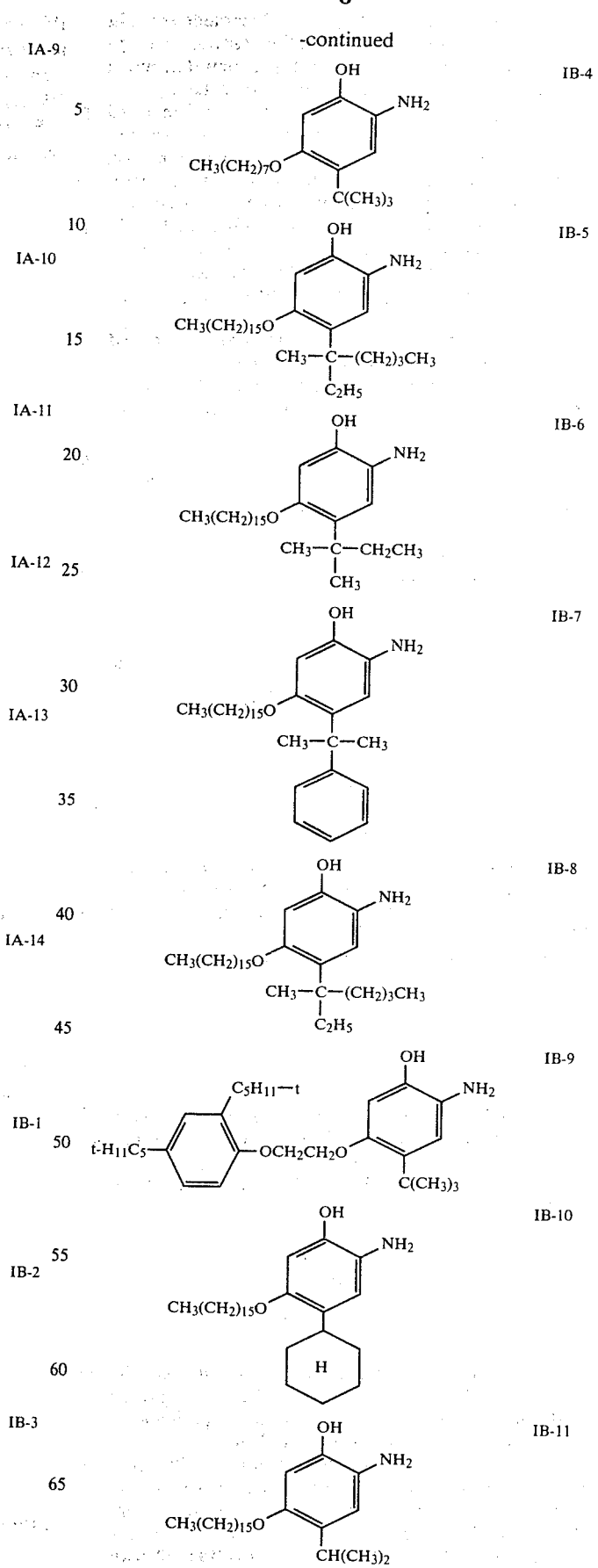

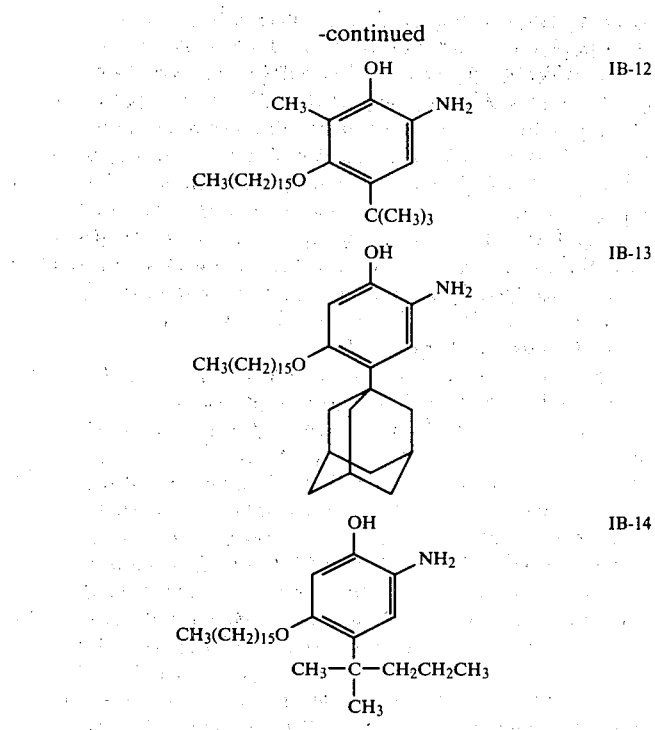

Representative processes for synthesizing the compounds represented by the formula (I) are shown below.

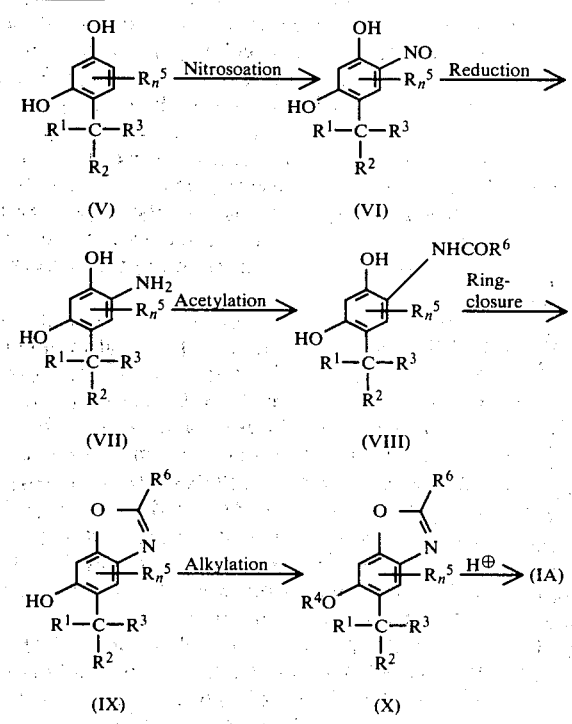

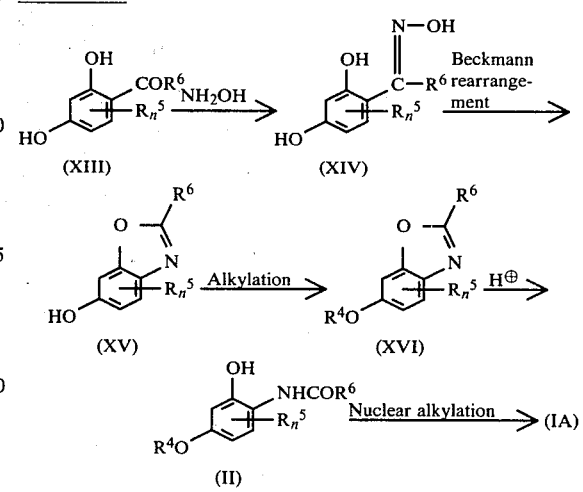

where each symbol represents the same meaning as defined in the formula (I).

In explanation of the Process I, a resorcinol derivative such as (V) is converted into a nitroso compound, which is then reduced and acetylated to obtain the compound (VIII). In these steps, operations described as a case of obtaining 2-acetamido-4-cyclohexylresorcinol from 4-cyclohexylresorcinol in W. M. McLamore, J. Amer. Chem. Soc., Vol. 73, pp. 2225–2230 (1951) can be utilized. Formation of the oxazole ring can be carried out by treating the compound (VIII) in the presence of an acid catalyst such as p-toluenesulfonic acid. The formation of the oxazole ring is referred to in the description of Japanese Patent Application (OPI) No. 153923/77. o-Alkylation of the oxazole derivative (IX) is generally carried out using $R^4$-X (where X is a halogen atom) and a basic substance such as sodium alkoxide or potassium carbonate as an agent for releasing hydrogen halide. This alkylation step is referred to in the description of Japanese Patent Application (OPI) No. 153923/77. The acetamide derivative (IA) can be obtained by ring opening of the oxazole ring in the compound (X).

In the Process II, a resorcinol derivative is subjected to nuclear acetylation (e.g., in the presence of BF$_3$-acetic acid), followed by reacting with hydroxylamine to prepare the oxime (XII). The compound (XII) is treated with phosphorus oxychloride or phosphorus pentachloride while blowing a hydrogen chloride gas into acetic acid, by which the Beckmann rearrangement and formation of oxazole can be carried out at the same time. The resulted compound (IX) is then treated by the same manner as that described in the above Process I to derive the compound (IA).

In the Process III, a 2,5-dihydroxyacetophenone derivative (a compound in which an acetyl group is replaced by another R$^6$CO group is, of course, useful as a starting material, but a compound having an acetyl group is preferred because it is easier to be synthesized) is subjected to reaction with hydroxylamine to produce the oxime (XIV). Then, the Beckmann rearrangement and formation of oxazole are carried out at the same time by the same manner as in case of the compound (XII) in the above Process II. In order to obtain the compound (XVI) by o-alkylation of the resulted oxazole (XV), R$^4$-X (wherein X is a halogen atom) is used and a basic substance such as sodium alkoxide or potassium carbonate is used as an agent for releasing hydrogen halide. This step for o-alkylation is referred to the description of Japanese Patent Application (OPI) No. 153923/77.

Then, the oxazole ring is opened by treating with diluted hydrochloric acid to obtain the compound (II). The compound represented by the formula (IA) can be synthesized by nuclear alkylation of the compound (II) by reacting with a moiety represented by the following formula (III) wherein R$^1$, R$^2$, and R$^3$ each have the same meaning as defined in the formula (I).

(III)

Among the Processes I, II and III, the Process III is particularly preferred because the synthesis operation is simple and the yield is high.

The moiety represented by the formula (III) is formed by reacting olefin (or alcohol or alkyl halide) with an acid catalyst. As the olefin used for this purpose, those represented by R$^1$R$^3$C=R$^{2a}$ (wherein R$^1$ and R$^3$ represent each the same meaning as defined in the formula (I) and R$^{2a}$ represents a group which produce R$^2$ by a proton addition) can be employed. For example, if isobutene is used as the olefin, a t-butyl group can be introduced. As the alcohol for forming the moiety (III), it is possible to use R$^1$R$^2$R$^3$C—OH (wherein R$^1$, R$^2$, and R$^3$ represent each the same meaning as defined in the formula (I)). The alkyl halide for forming the moiety (III) is represented by the formula R$^1$R$^2$R$^3$C-X (wherein R$^1$, R$^2$, and R$^3$ each have the same meaning as defined in the formula (I) and X represents a halogen atom). Catalysts capable of being used for the nuclear alkylation include Brönsted acids, such as sulfuric acid or phosphoric acid, etc.; Lewis acids, such as aluminium chloride, boron trifluoride or ether complex thereof, zinc chloride, iron chloride, titanium chloride or antimony pentachloride, etc.; clay minerals, such as acid clay, bentonite or kaolin, etc.; and solid acids, including silica-alumina catalysts, solid acids produced by attaching sulfuric acid or phosphoric acid to diatomaceous earth or silica sand, and solid acids including ionexchange resins such as Amberlite IR-120 (H), Amberlite IR-112 (H) and Amberlite 15 (which are trademarks of Rhom & Haas Co., U.S.A.), etc. Details of these catalysts and other examples are described in *San-Enki Shokubai* (*Acid and Base Catalysts*), by Kozo Tabe and Tsuneichi Takeshita, pp. 23-224, published by Sangyo Tosho Co., Tokyo (1966). Reaction conditions for nuclear alkylation are described in *Friedel-Crafts and Related Reactions*, Vol. II, Alkylation and Related Reaction, edited by G. A. Olah, Interscience Publishers, New York (1964) and *Chem. and Eng. News*, 112, Jan. 25 (1965), by R. M. Roberts.

When generating the moiety (III) using the olefin R$^1$R$^3$C=R$^{2a}$, followed by nuclear alkylation of the compound (II), the olefin R$^1$R$^3$C=R$^{2a}$ is used in an amount of 1 mol to 100 mols, preferably 1 mol to 50 mols, and particularly 1 mol to 20 mols, per mol of the compound (II). In this case, as the catalyst, it is particularly preferred to use solid acids comprising ion-exchange resins such as Amberlist 15, Lewis acids such as boron trifluoride (and ether complex thereof), and Brönsted acids such as sulfuric acid or phosphoric acid, etc. The catalyst is preferably used in an amount of from 0.1 to 100 parts by weight, more preferably in an amount from 0.5 to 50 parts by weight, and most preferably in an amount from 0.5 to 20 parts by weight, per part by weight of the compound (II). The reaction temperature depends upon the kind of olefin R$^1$R$^3$C=R$^{2a}$ and the kind of catalyst used, but it is generally preferred to be within the range of from −20° C. to 300° C., more preferably from 0° C. to 200° C., and most preferably from 0° C. to 150° C. In the case of using the solid acid, it is preferred to use, as a solvent, aromatic hydrocarbons such as toluene or benzene, etc., and halogenated hydrocarbons such as 1,2-dichloroethane or 1,1,1-trichloroethane, etc. Further, as a solvent in the case of using the Lewis acid, it is preferred to use halogenated hydrocarbons, such as 1,2-dichloroethane or 1,1,1-trichloroethane, and so forth. As a solvent in case of using Brönsted acid, it is preferred to use ester type solvents such as ethyl acetate, etc., and the above-described halogenated hydrocarbons. However, if the olefin or the catalyst is liquid at a reaction temperature, the reaction can be carried out without using the solvent.

In the case of generating the moiety (III) with using the alcohol R$^1$R$^2$R$^3$C—OH, followed by alkylation of the compound (II), the alcohol R$^1$R$^2$R$^3$C—OH is used in an amount of from 1 to 100 mols, preferably in an amount from 1 to 50 mols, and most preferably in an amount from 1 to 20 mols, per mol of the compound (II). In this case, as the catalyst, Brönsted acids such as sulfuric acid or phosphoric acid, etc., are particularly preferred to use. The catalyst is preferably used in an amount of from 0.1 to 100 parts by weight, more preferably in an amount from 0.5 to 50 parts by weight, and most preferably in an amount from 1 to 20 parts by weight, per part by weight of the compound (II). The reaction temperature depends upon the kind of alcohol and the kind of catalyst, but it is generally preferred to be in the range of from 0° C. to 300° C., more preferably from 20° C. to 200° C., and most preferably from 20° C. to 150° C. As a solvent, it is preferred to use ester type solvents such as ethyl acetate, and halogenated hydrocarbons such as 1,2-dichloroethane or 1,1,1-trichloroethane, etc., but the reaction can be carried out without using solvent.

In the case of generating the moiety (III) using the alkyl halide $R^1R^2R^3C-X$, followed by nuclear alkylation of the compound (II), the alkyl halide $R^1R^2R^3C-X$ is used in an amount of from 1 to 100 mols, more preferably in an amount from 1 to 50 mols, and most preferably in an amount from 1 to 20 mols, per mol of the compound (II). In this case, Lewis acids such as zinc chloride, boron trifluoride (and ether complex thereof) or iron chloride, etc., are preferred for use as the catalyst. The catalyst is preferably used in an amount of from 0.05 to 100 parts by weight, more preferably in an amount from 0.1 to 50 parts by weight, and most preferably in an amount from 0.1 to 20 parts by weight, per part by weight of the compound (II). The reaction temperature depends upon the kind of alkyl halide $R^1R^2R^3C-X$ and the kind of catalyst, but it is generally preferred to be in the range of from 0° C. to 300° C., more preferably from 20° C. to 200° C. and most preferably from 20° C. to 150° C. As a solvent, it is preferred to use halogenated hydrocarbons such as 1,2-dichloroethane or 1,1,1-trichloroethane, etc., and liquid carboxylic acids such as acetic acid, etc.

Some examples of the compounds according to the invention are illustrated below.

SYNTHESIS EXAMPLE 1

Synthesis of 6-hydroxy-2-methylbenzoxazole (formation of oxazole ring by Beckmann rearrangement)

306 g of 2,4-dihydroxyacetophenone, 164 g of hydroxylamine hydrochloride, 328 g of sodium acetate, 1,000 ml of ethanol and 500 ml of water were blended and the mixture was refluxed with heating for 4 hours. The reacting solution was poured into 10 liters of water and the crystals formed were separated by filtration to obtain 314 g of oxime.

100 g of the resulted 2,4-dihydroxyacetophenone oxime was dissolved in 700 ml of acetic acid and a hydrogen chloride gas was introduced thereto by blowing for 2.5 hours with stirring under heating to a temperature from about 120° to 140° C. After cooling, the crystals formed were separated by filtration and washed then with water to obtain 62 g of 6-hydroxy-2-methylbenzoxazole.

SYNTHESIS EXAMPLE 2

Synthesis of 6-hexadecyloxy-2-methylbenzoxazole (O-alkylation)

A mixture composed of 18.0 g of 6-hydroxy-2-methylbenzoxazole synthesized in Synthesis Example 1, 36.6 g of 1-bromohexadecane, 24.0 g of potassium carbonate and 120 ml of N,N-dimethylformamide was stirred at 90° C. for 4.5 hours. Solids were removed from the reacting solution by filtration, and the filtrate was poured into 500 ml of methanol. The crystals formed were separated by filtration to obtain 45.0 g of 6-hexadecyloxy-2-methylbenzoxazole.

SYNTHESIS EXAMPLE 3

Synthesis of 2-acetylamino-5-hexadecyloxyphenol (ring opening of oxazole ring)

111 g of 6-hexadecyloxy-2-methylbenzoxazole obtained in Synthesis Example 2, 1,300 ml of ethanol, 110 ml of 35% hydrochloric acid and 550ml of water were blended, and the mixture was stirred for 4 hours at about 55° to 60° C. After cooled, the crystals formed were separated by filtration to obtain 113 g of 2-acetylamino-5-hexadecyloxyphenol.

EXAMPLE 1

Synthesis of 2-acetylamino-4-t-butyl-5-hexadecyloxyphenol (Compound IA-1) (nuclear alkylation)

30.0 g of 2-acetylamino-5-hexadecyloxyphenol obtained in Synthesis Example 3, 20.0 g of Amberlist 15 (trademark of Rohm & Haas Co., U.S.A.) and 300 ml of toluene were blended. Isobutene was circulated for 5 hours with stirring under heating to about 80° to 90° C. After removal of solid substances by filtration, the filtrate was condensed, and 350 ml of n-hexane was added to the residue. The crystals thus-formed were separated by filtration to obtain 23.5 g of 2-acetylamino-4-t-butyl-5-hexadecyloxyphenol.

EXAMPLE 7

Synthesis of 2-acetylamino-4-(α,α-dimethylbenzyl)-5-hexadecyloxyphenol (Compound IA-7)

20 g of -acetylamino-5-hexadecyloxyphenol obtained in Synthesis Example 3 was dissolved in 150 ml of toluene, and the solution was heated to a temperature from about 80° to 90° C. together with 8 g of Amberlist 15 (trademark of Rohm & Haas Co., U.S.A.). To the mixture, 30 ml of α-methylstyrene was added dropwise, and the mixture was heated for about 7 hours. After conclusion of the reaction, Amberlist 15 was removed by filtration and the filtrate was condensed. Methanol was added thereto and the solution was cooled with ice, by which the desired product was separated. It was separated by filtration and washed well with methanol. Yield: 6.6 g.

EXAMPLE 3

Synthesis of 2-acetylamino-4-(1-ethyl-1-methylpentyl)-5-hexadecyloxyphenol (Compound IA-5)

A mixture composed of 25 g of 2-aceytylamino-5-hexadecyloxyphenol, 250 ml of 2-ethyl-1-hexene, 100 g of Amberlist 15 and 750 ml of toluene was stirred for 4 hours with heating to 80° C. Amberlist 15 was then removed by filtration and toluene was removed from the filtrate by distillation. To the residue, 150 ml of hexane was added and the solution was cooled for 8 hours with ice. The resulted crystals were taken out by filtration and washed with hexane, followed by drying in the air. Yield: 6.0 g.

With using the compounds of the present invention as intermediates, dye-releasing redox compounds suitable for a color diffusion transfer process can be synthesized. Typical examples of these redox compounds include compounds represented by the following formula (XVII).

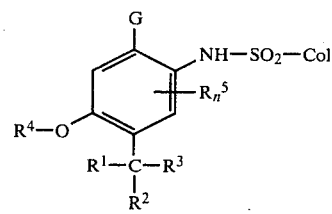

(XVII)

wherein $R^1$, $R^2$, $R^3$, $R^4$, $R^5$, and n represent each the same meaning as defined in the formula (I), G represents a hydroxyl group or a group which forms a hydroxyl group by hydrolysis, and Col represents a dye or a dye precursor.

Examples of G include groups represented by Alkyl—COO— having from 2 to 40 carbon atoms, preferably from 2 to 8 carbon atoms and particularly from 2 to 4 carbon atoms (for example, an acetoxy group or a propionyloxy group, etc.) and aromatic carbonyloxy groups having from 6 to 40 carbon atoms, preferably from 6 to 15 carbon atoms and particularly from 6 to 9 carbon atoms (for example, a benzoyloxy group or a substituted benzoyloxy group, etc.).

Examples of Col include azo dyes, azomethine dyes, indoaniline dyes, indophenol dyes, triphenylmethane dyes, anthraquinone dyes, indigo dyes and metal complex salts of them and dye precursors which form these dyes by hydrolysis such as those having an acylated auxochrome of dyes as described in, for example, Japanese Patent Application (OPI) No. 125818/73 and U.S. Pat. Nos. 3,222,196 and 3,307,947. The dye precursors are particularly preferred for temporarily moving the absorption of dyes to a shorter wavelength side during exposure for the purpose of preventing desensitization caused by light absorption in case of applying these dye image-forming agents together with a photosensitive emulsion as a mixture. Further, it is possible for this purpose to use dyes the color of which is different in case of transferring on a mordant from that in case of being contained in the emulsion layer. Further, the Col part may have groups of providing solubility in water such as carboxyl and sulfonamide groups.

The dye-releasing redox compounds obtained with using the compounds of the present invention are necessary to have a ballast group by which said compounds become substantially nondiffusible or do not flow, in order to prevent diffusion or flowing thereof by alkalis used at development of the sensitive materials. The size of group and the number of carbon atoms required for the ballast group depend upon the conditions used, for example, the treating time, the concentration of alkali, and the number of water-solubilizing group in the Col part, but $R^1$, $R^2$, $R^3$, $R^4$, and $R^5_n$ must have a total of 7 or more carbon atoms. Though it becomes less advantageous from the viewpoint of the solubility or light absorption coefficient as the number of carbon atoms increases, there is theoretically no maximum number of carbon atoms. Generally, $R^1$ through $R^5_n$ have a total of from 7 to 80 carbon atoms, and preferably from 13 to 40 carbon atoms.

In Research Disclosure, No. 13024 (1975), 6-sulfonamidophenols have been described, in which it has been shown that 2-sulfonamidophenols having an alkyl group on the 5-position hardly have a development activity and, consequently, they do not release a dye. In the dye-releasing redox compounds obtained with using the compounds of the present invention, it is obvious that variation of important photographic properties is caused by linking the group $R^4O$— to 5-position of phenol and linking a secondary or tertiary alkyl group (namely, the group $R^1R^2R^3C$—) to 4-position. The dye-releasing redox compounds obtained using the compounds of this invention are excellent as compared with dye-releasing redox compounds described in Japanese Patent Application (OPI) Nos. 113624/76 and 149328/78, since a side reaction of hydrolysis in the oxidation product and of other steps (e.g., oxidation of the DRR compounds) is prevented by steric hindrance of the secondary or tertiary alkyl group ($R^1R^2R^3C$—) and the dye-releasing efficiency is improved. Accordingly, the oxidized compounds effectively release a diffusible dye without fail.

The dye-releasing redox compounds obtained using the compounds of this invention form o-quinoneimide by a redox reaction during development, and the o-quinoneimide is hydrolyzed to release a sulfonamide part. The formed o-benzoquinone is believed to cause less residual color after releasing the dye because it has only light color absorption as compared with the abovedescribed naphthoquinones.

The dye-releasing redox compounds obtained using the compounds of the present invention are used for photosensitive materials for a color diffusion transfer process similarly to the case of dye-releasing redox compounds described in Japanese Patent Application (OPI) No. 113624/76, etc.

Particularly preferred dye-releasing redox compounds obtained using the compounds of this invention are represented by the following formula (XVIII)

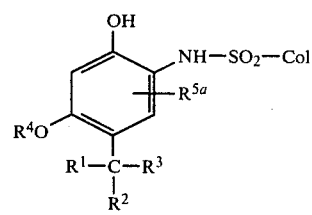

(XVIII)

wherein $R^1$, $R^2$, $R^3$, $R^4$, and Col each represent the same meaning as defined in the formula (XVII), and $R^{5a}$ represents the same meaning as defined in the formula (IV).

Examples of dye-releasing redox compounds in the present invention represented by the formula (XVII) are shown in the following.

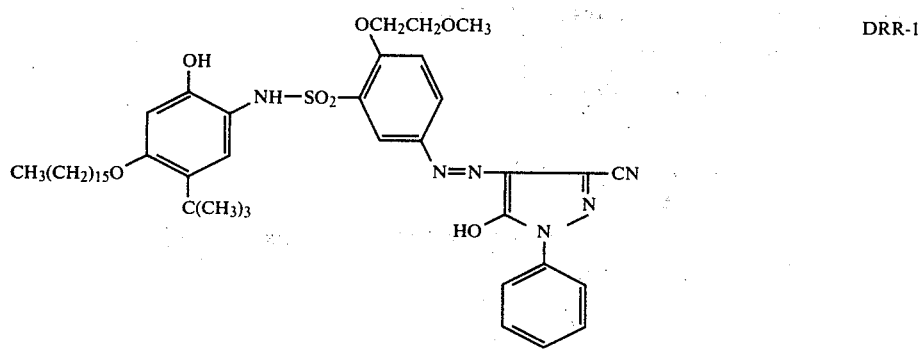
DRR-1
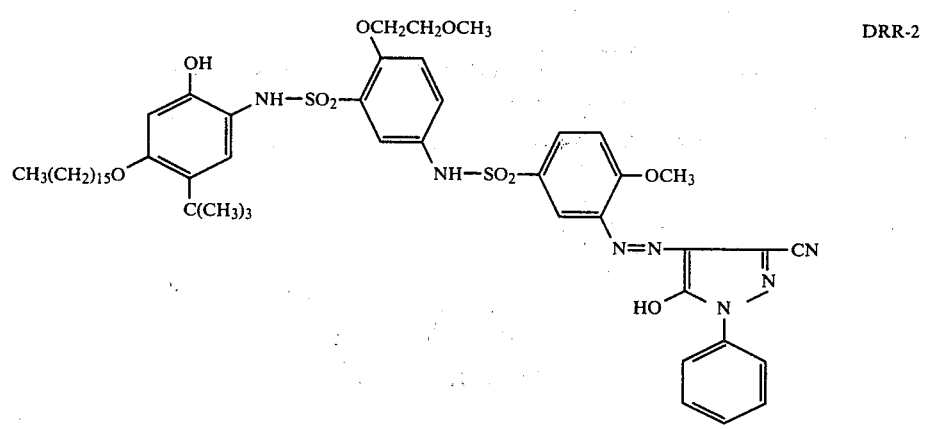
DRR-2
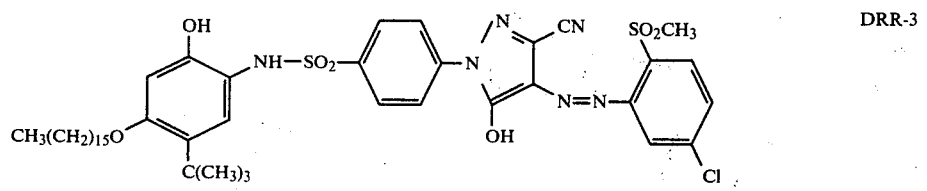
DRR-3
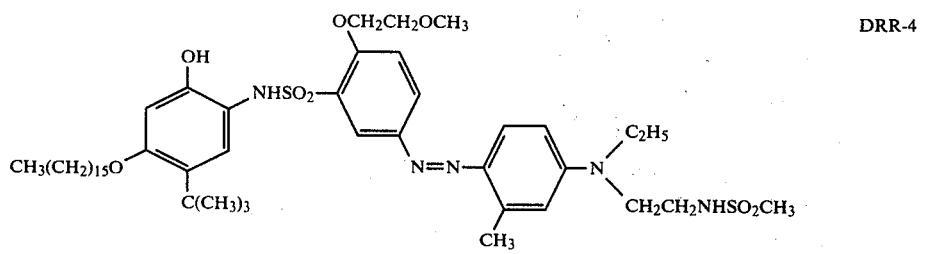
DRR-4
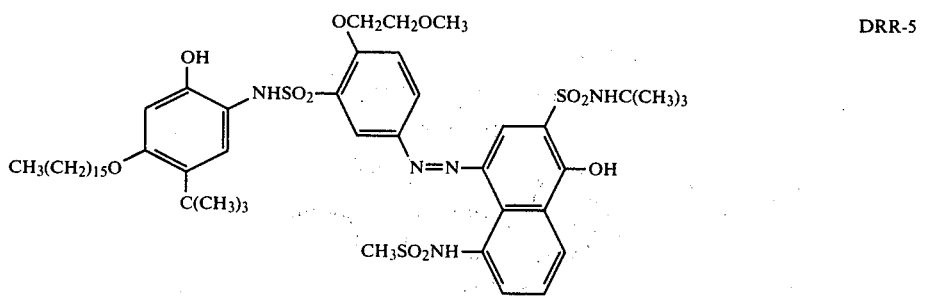
DRR-5

-continued
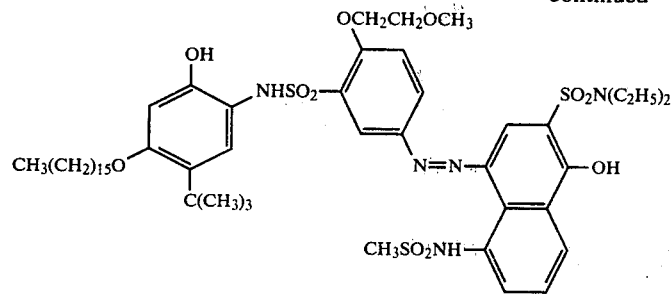
DRR-6
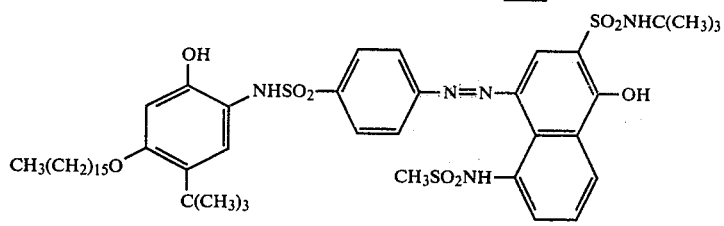
DRR-7
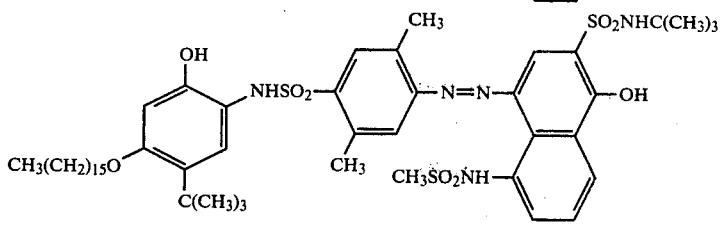
DRR-8
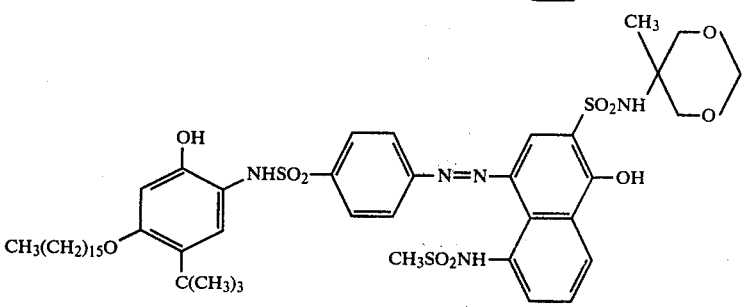
DRR-9
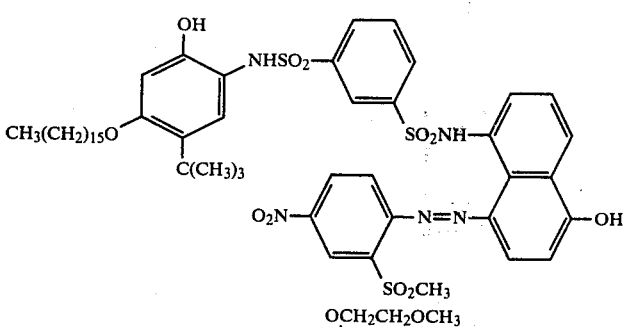
DRR-10
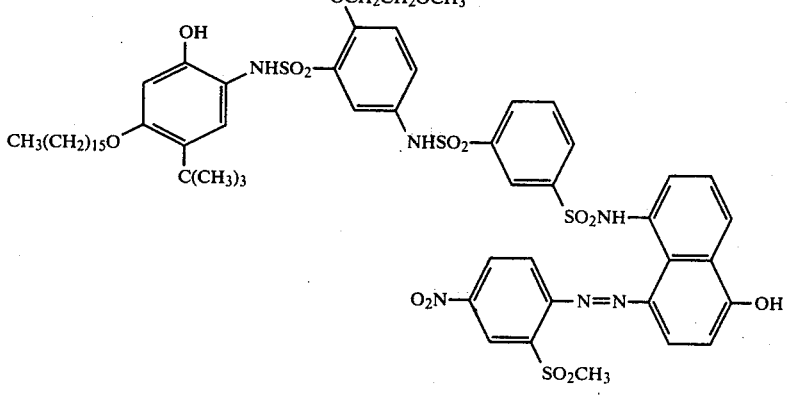
DRR-11

-continued
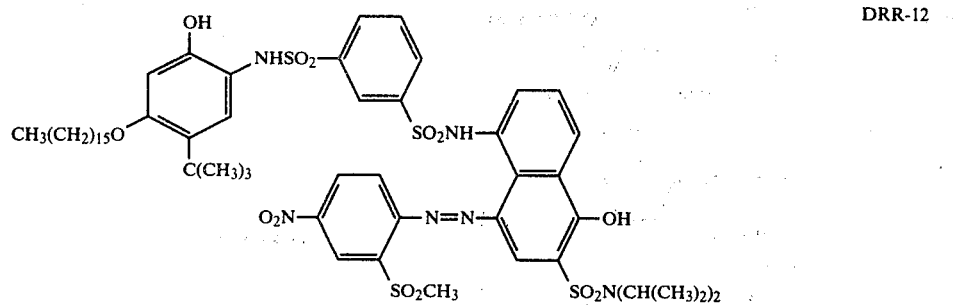
DRR-12
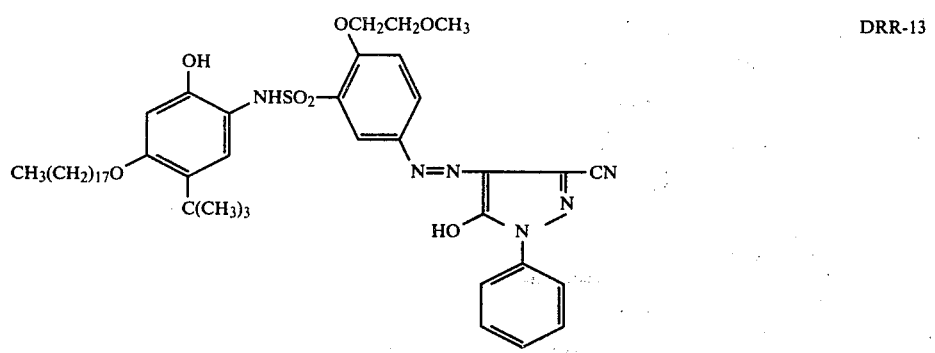
DRR-13
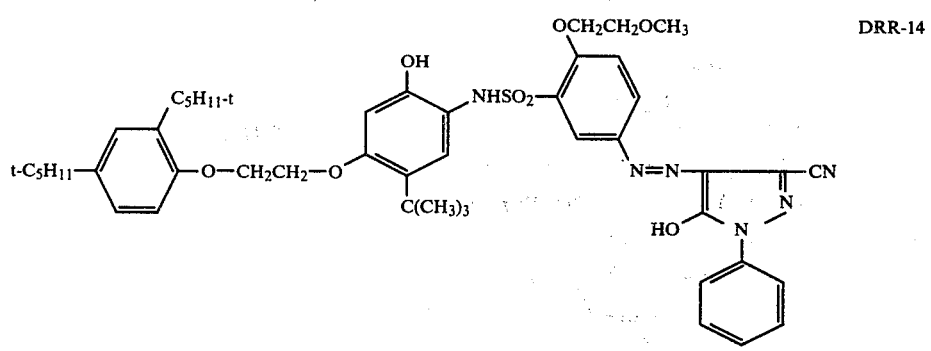
DRR-14
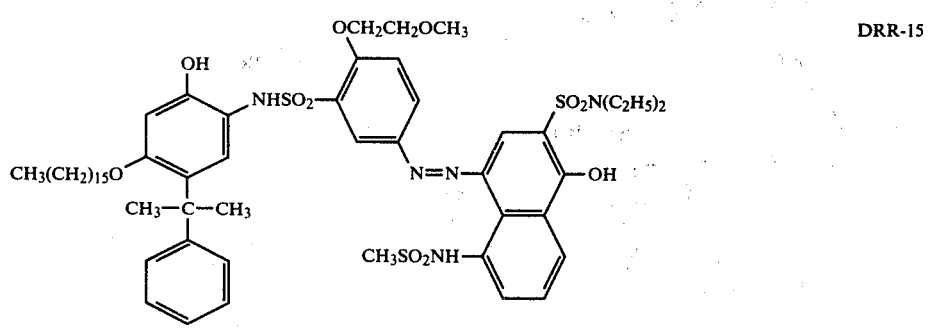
DRR-15
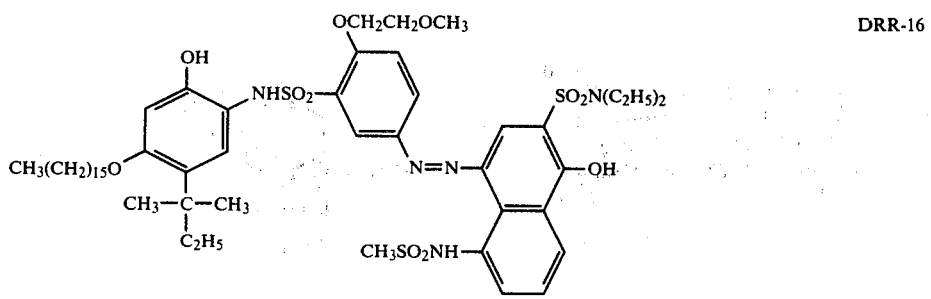
DRR-16

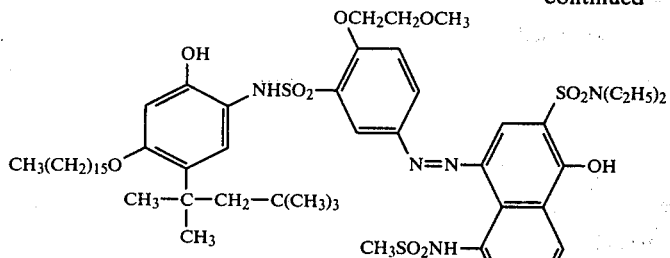
DRR-17
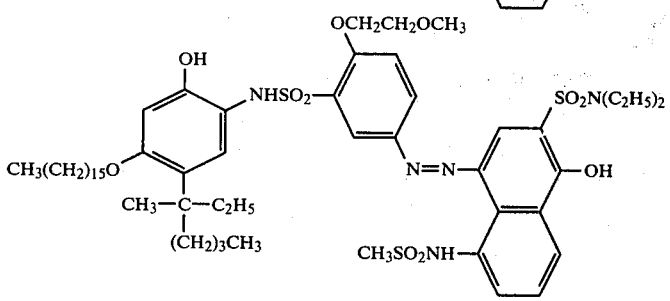
DRR-18
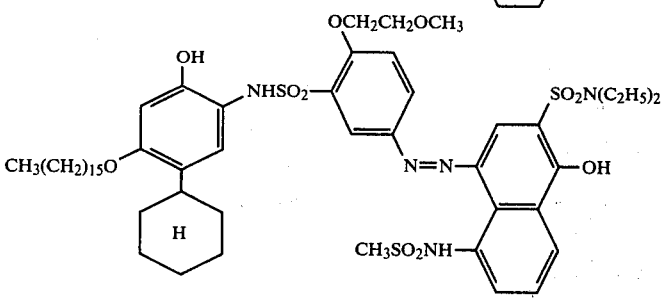
DRR-19
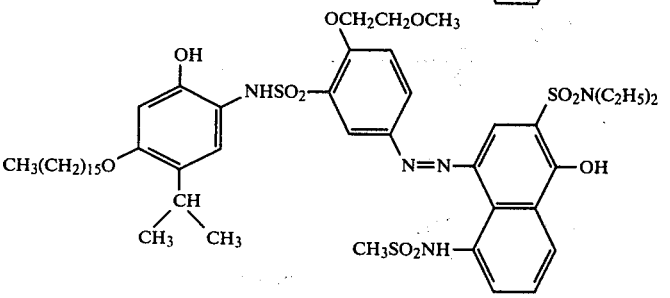
DRR-20
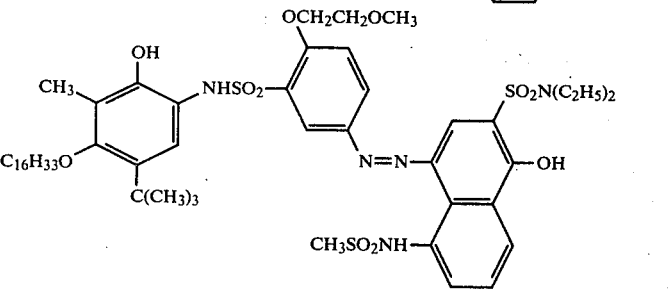
DRR-21
The compounds represented by the formula (XVII) in the present invention can be synthesized, in general, by a condensation reaction of sulfonyl halide of azo dyes (XIX) with o-aminophenol derivatives having various organic ballast group (IB).
Col-SO₂X       (XIX)
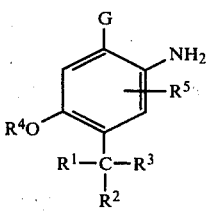
(IB)

wherein X represents a halogen atom, and the other symbols each have the same meaning as defined in the formula (I).

A process for synthesizing dye parts and sulfonyl halide thereof (XIX) has been described in Japanese Patent Application (OPI) Nos. 12581/73, 33826/73, 114424/74 and 126332/74.

The compounds represented by the formula (IB) can be obtained by hydrolyzing the compounds (IA) of the present invention. Hydrolysis is easily carried out by a process which comprises treating with acids such as diluted hydrochloric acid. Examples are shown below.

EXAMPLE 4

Synthesis of 2-amino-4-t-butyl-5-hexadecyloxyphenol (IB-1) hydrochloride (deacetylation)

23.0 g of 2-acetylamino-4-t-butyl-5-hexadecyloxyphenol obtained in Example 1, 120 ml of ethanol and 96 ml of 35% hydrochloric acid were blended, and the mixture was refluxed for 5 hours with stirring. After cooling the reaction solution, the crystals formed were separated by filtration to obtain 23.2 g of 2-amino-4-t-butyl-5-hexadecyloxyphenol hydrochloride.

EXAMPLE 5

Synthesis of 2-amino-4-(α,α-dimethylbenzyl)-5-hexadecyloxyphenol (IB-7) hydrochloride 6.4 g of the compound obtained in Example 2 was refluxed for 3 hours together with 45 ml of ethanol and 30 ml of concentrated hydrochloric acid. After conclusion of the reaction, the solution was cooled and the crystals formed were separated by filtration. Yield: 6.1 g.

EXAMPLE 6

Synthesis of 2-amino-4-(1-ethyl-1-methylpentyl)-5-hexadecyloxyphenol (IB-5) hydrochloride 30 ml of ethanol and 25 ml of concentrated hydrochloric acid were added to 6 g of 2-acetamido-4-(1-ethyl-1-methylpentyl)-5-hexadecyloxyphenol obtained in Example 3 and the mixture was heated for 4 hours on a steam bath. The reacting solution was then cooled by which two phases were separated. The oil phase was separated and dried in vacuum. Yield: 3.5 g.

The compounds represented by the formula (IA) may be synthesized by condensing the above-described compounds represented by the formula (IB) with $R^6COCl$ in a presence of a base, too. This reaction can be carried out under the same conditions as that of a condensation reaction of compounds (IB) with compounds (XIX), as described hereinafter.

The condensation reaction of the compounds (XIX) with the compounds (IB) is generally preferred to be conducted in a presence of a basic substance. Examples of such basic substances include hydroxides of alkali metals or alkaline earth metals (for example, sodium hydroxide, potassium hydroxide, barium hydroxide and calcium hydroxide, etc.), aliphatic amines (for example, triethylamine, etc.), aromatic amines (for example, N,N-diethylaniline, etc.), heteroaromatic amines (for example, pyridine, quinoline, α-, β- and γ-picolines, lutidines and collidines, and 4-(N,N-dimethylamino)-pyridine, etc.) and heterocyclic bases (for example, 1,5-diazabicyclo[4,3,0]nonene-5 and 1,8-diazabicyclo[5,4,0]-undecene-7, etc.). When X is chlorine, namely, the formula (XIX) is sulfonyl chloride, the heteroaromatic amines (preferably pyridine) are advantageous. An example of synthesizing the dye-releasing redox compounds using an intermediate compound of the present invention is described below.

SYNTHESIS OF COMPOUND DRR-1

(a) Synthesis of sodium 2-(2-methoxyethoxy)-5-nitrobenzenesulfonate

To a solution of sodium 2-methoxy-ethylate prepared by adding 7.3 g of sodium hydride (14.6 g as a state of 50% liquid paraffin dispersion) to 300 ml of methyl cellosolve, 55 g of sodium 2-chloro-5-nitrobenzenesulfonate was added with stirring. The reaction mixture was heated to a temperature from about 80° to 85° C. in a hot water bath with stirring for 30 minutes. After carried out filtration with heating, 1.5 liters of isopropyl alcohol were added to the filtrate. The crystals thus-formed were separated by filtration and washed with 100 ml of isopropyl alcohol. Yield: 59 g. m.p.: 238°–239° C.

(b) Synthesis of 5-amino-2-(2-methoxyethoxy)benzenesulfonic acid

A mixture composed of 30 g of 2-(2-methoxyethoxy)-5-nitrobenzenesulfonic acid, 30 g of reduced iron, 0.6 g of ammonium chloride and 60 ml of water was kept at about 80° to 85° C. and stirred for 2 hours. After conclusion of the reaction, insoluble materials were removed by filtration, and 200 ml of isopropyl alcohol was added to the filtrate, which was cooled with ice. The crystals thus-formed were separated by filtration, washed with 50 ml of isopropyl alcohol and dried in the air. Yield: 23 g. m.p.: more than 250° C.

(c) Synthesis of 3-cyano-4-(4-methoxyethoxy-5-sulfophenylazo)-1-phenyl-5-pyrazolone To a solution composed of 8.0 g of sodium hydroxide and 200 ml of water, 49.4 g of 5-amino-2-(2-methoxyethoxy)benzenesulfonic acid was added, and an aqueous solution (50 ml) of 13.8 g of sodium nitrite was added thereto. On the other hand, 60 ml of concentrated hydrochloric acid was diluted with 400 ml of water to prepare hydrochloric acid. This hydrochloric acid was added dropwise at less than 5° C. Thereafter, the resulted mixture was stirred at less than 5° C. for 30 minutes to conclude the reaction (this solution is referred to as the diazo solution).

On the other hand, 37.0 g of 3-cyano-1-phenyl-5-pyrazolone was added to a mixture composed of 16.0 g of sodium hydroxide, 200 ml of water, 33.0 g of sodium acetate and 200 ml of methanol. Then the above-described diazo solution was added dropwise at less than 10° C. After conclusion of the addition, the mixture was stirred at less than 10° C. for 30 minutes. After stirred at a room temperature for 1 hour, separated crystals were taken out by filtration, washed with 200 ml of acetone and dried in the air. Yield: 52.0 g. m.p.: 263°–265° C.

(d) Synthesis of 3-cyano-4-(4-methoxyethoxy-5-chlorosulfonylphenylazo)-1-phenyl-5-pyrazolone 50 ml of N,N-dimethylacetamide was added dropwise to a mixture composed of 51.0 g of 3-cyano-4-(4-methoxyethoxy-5-sulfophenylazo)-1-phenyl-5-pyrazolone obtained in the above (C), 250 ml of acetone and 50 ml of phosphorus oxychloride at less than 50° C. After addition, the mixture was stirred for about 1 hour and poured slowly into 1.0 liter of ice water. The crystals formed were separated by filtration, washed with 100 ml of acetonitrile and dried in the air. Yield: 46.7 g. m.p.: 181°–183° C.

(e) Synthesis of Compound DRR-1

4.4 g of 2-amino-4-t-butyl-5-hexadecyloxy-5-methylphenol hydrochloride obtained in Example 4 and 4.6 g of 3-cyano-4-(4-methoxyethoxy-5-chlorosulfonylphenylazo)-1-phenyl-5-pyrazolone obtained in the above (d) were added to 20 ml of N,N-dimethylacetamide. To the resulting mixture, 4.7 ml of pyridine was added dropwise while stirring the mixture. After addition it was further stirred at a room temperature for 2 hours. After stirred, 30 ml of methanol and 10 ml of water were added to the reaction solution. To the separated oily substance, about 20 ml of ethanol was added, to form crystals which were separated by filtration. Yield: 4.8 g.

While the invention has been described in detail and with reference to specific embodiments thereof, it will be apparent to one skilled in the art that various changes and modifications can be made therein without departing from the spirit and scope thereof.

What is claimed is:

1. An o-aminophenol compound represented by the formula (IB)

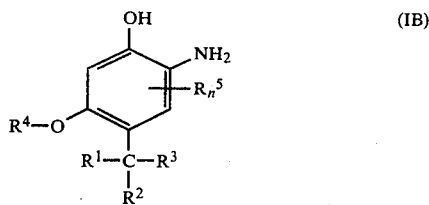

wherein:

$R^1$ and $R^2$, which may be the same or different, each represent an alkyl group or an aromatic group, or $R^1$ and $R^2$ together can form a ring, or $R^1$, $R^2$ and $R^3$ together can form a ring;

$R^3$ represents hydrogen atom, an alkyl group or an aromatic group;

$R^4$ can represent an alkyl group or an aromatic group;

$R^5$ can represent an alkyl group, an alkoxy group, an alkylthio group, an arylthio group, a halogen atom or an acylamino group, and n is 0, 1 or 2; and $R^4$ and $R^5$ together can form a heterocyclic ring, $R^1$ and $R^4$ together can form a heterocyclic ring, or $R^1$ and $R^5$ together can form a ring; and $R^1$, $R^2$, $R^3$, $R^4$, and $R^5_n$ contain a total of 7 or more carbon atoms.

2. An o-aminophenol compound as claimed in claim 1, wherein $R^1$ and $R^2$ independently represent an alkyl group;

$R^3$ represents hydrogen or an alkyl group;

$R^4$ represents an alkyl group;

$R^5$ represents an alkyl group, an alkoxy group, an alkylthio group, a halogen atom, and n is 0, 1 or 2;

$R^1$, $R^2$, $R^3$, $R^4$, and $R^5_n$ contain a total of 7 or more carbon atoms.

3. An o-aminophenol compound as in claim 1, wherein the alkyl groups represented by $R^1$, $R^2$, $R^3$, and $R^4$ contain from 1 to 40 carbon atoms.

4. An o-aminophenol compound as in claim 3, wherein the alkyl groups represented by $R^1$, $R^2$, $R^3$, and $R^4$ contain from 1 to 24 carbon atoms.

5. An o-aminophenol compound as in claim 1, wherein the aromatic groups represented by $R^1$, $R^2$, $R^3$, and $R^4$ are selected from the group consisting of a phenyl group, a substituted phenyl group, a naphthyl group, and a substituted naphthyl group.

6. An o-aminophenol compound as in claim 1, wherein the alkyl group, the alkoxy group, or the alkylthio group represented by $R^5$ contains from 1 to 40 carbon atoms.

7. An o-aminophenol compound as in claim 6, wherein the alkyl group, the alkoxy group, or the alkylthio group represented by $R^5$ contains from 1 to 24 carbon atoms.

* * * * *